Oct. 18, 1932.
R. ENGLE
Plant Pat. 35
CARNATION
Filed Jan. 29, 1932
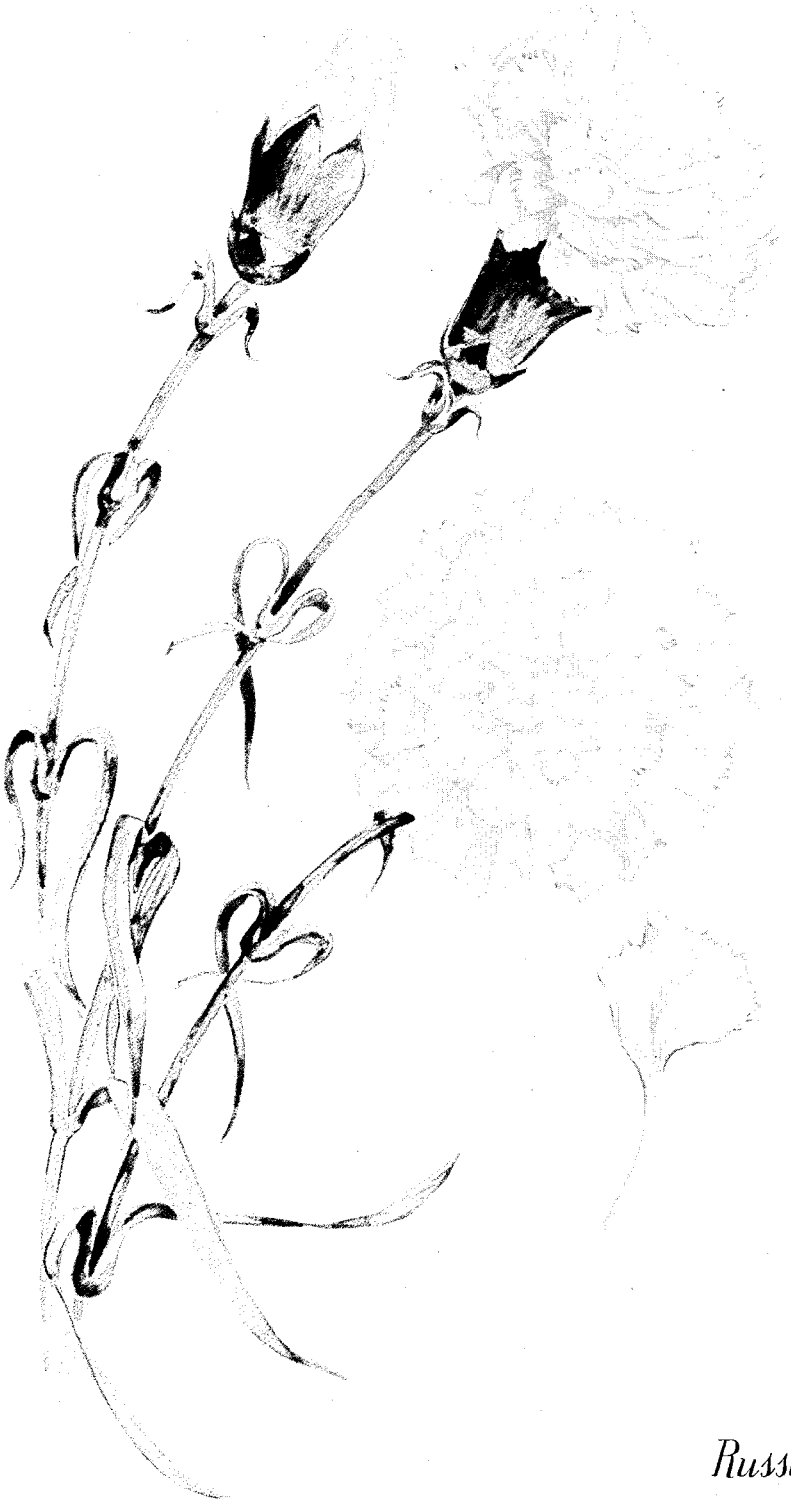
Inventor
*Russell Engle*
By *E. Y. Bradford*
Attorney Patented Oct. 18, 1932

Plant Pat. 35

UNITED STATES PATENT OFFICE

RUSSELL ENGLE, OF KOKOMO, INDIANA, ASSIGNOR TO THOMAS L. KNIPE, OF KOKOMO, INDIANA

CARNATION

Application filed January 29, 1932. Serial No. 589,702.

This invention relates to improvements in carnations and consists in the production of a carnation having new and richer colors than carnations heretofore known and one which is practically immune to the diseases common to carnations.

The following description and accompanying drawing illustrate my new carnation in so far as it is possible to produce the colors in a mechanical way.

The drawing shows a carnation having blossoms in three stages of development, from a bud just opening to the full flower, and also show a single petal of a blossom from my new carnation.

Among florists and nurserymen there is a continual quest for new and improved varieties of flowers and plants and particularly for new and richer colors in flowers and for more vigorous plants. My new carnation possesses a new color or combination of colors which are the result of long experimental work in attempting to make improvements in flowers.

My new plant was produced by cross breeding. The pollen from an unnamed seedling producing white blooms was transferred by hand to the pistils of the flowers of a cream colored carnation known as Early Dawn. My plant was raised from the seed resulting from this cross breeding. The new variety must be propagated by cuttings from the original plant.

In coloring the flower is variegated and somewhat brighter in color at one side of the bloom than at the other. Many of the petals are of a golden-peach color shot through with flame color. The petals are fringed with a rather lighter flame. The flower is somewhat more double than the pictures show since it was rather difficult to depict the full double characteristic of the flower and bring out clearly the combination of colors.

The flower grows and produces freely and has stems medium tall or average in length which are stiff enough to hold the flowers gracefully. The flowers are very large and double and full and measure from 3 to 4 inches in diameter. The calyx never splits.

I have found through a long experimentation and under close observation that the flower is not subject to diseases that are more common to plants and that usually attack carnations. In the locality where it has been developed it has been found up until now to be apparently immune to the more common diseases that attack carnations.

This carnation has not been sold or otherwise given to the public.

Having thus fully described and illustrated my new plant, what I claim as new and desire to secure by Letters Patent, is:

The carnation as shown and described characterized in unusually large flowers, the petals of which are generally a rich cream in color and streaked and tinged with flame and with pink.

In witness whereof, I have hereunto set my hand at Kokomo, Indiana, this 18th day of January, A. D. nineteen hundred and thirty-two.

RUSSELL ENGLE.